United States Patent [19]

Gesellchen

[11] 4,309,343
[45] Jan. 5, 1982

[54] PHARMACOLOGICALLY ACTIVE PEPTIDES

[75] Inventor: Paul D. Gesellchen, Indianapolis, Ind.

[73] Assignee: Eli Lilly and Company, Indianapolis, Ind.

[21] Appl. No.: 210,210

[22] Filed: Nov. 25, 1980

[51] Int. Cl.³ .......................................... C07C 103/52
[52] U.S. Cl. ............................................. 260/112.5 E
[58] Field of Search ................................ 260/112.5 E

[56] References Cited

U.S. PATENT DOCUMENTS 4,180,501 12/1979 Coy et al. ..................... 260/112.5 E

OTHER PUBLICATIONS

Hughes et al., Nature, 258, 577, (1975).
Buscher et al., Nature, 261, 423, (1976).
Dutta et al., Life Sciences, 21, pp. 559–562, (1977).
Roemer et al., Nature, 268, 547–549, (1977).
Coy et al., Biochem. and Biophys. Comm., 83, 977–983, (1978).

*Primary Examiner*—Delbert R. Phillips
*Attorney, Agent, or Firm*—William C. Martens; Arthur R. Whale

[57] ABSTRACT

Compounds of the formula

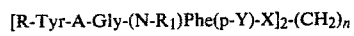

in which
R is hydrogen or methyl;
A is the residue of a D-amino acid selected from the group consisting of Ala, Abu, Ser, Thr, and Met;
$R_1$ is hydrogen, $C_1$–$C_3$ primary alkyl, cyclopropylmethyl, or allyl;
Y is hydrogen or fluoro;
n is an integer from 1 to 10; and
X is —NH— or a group of the formula

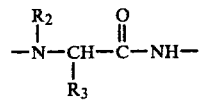

in which $R_2$ is hydrogen or $C_1$–$C_3$ primary alkyl; $R_3$ is phenyl, 2-methylthioethyl, or isobutyl; or $R_2$ and $R_3$ taken together are —$CH_2$—$CH_2$—$CH_2$—;

subject to the limitation that, when $R_2$ is other than hydrogen, $R_1$ is hydrogen; are useful analgesic agents.

41 Claims, No Drawings

PHARMACOLOGICALLY ACTIVE PEPTIDES

BACKGROUND OF THE INVENTION

This invention relates to a novel class of compounds which exhibit analgesic activity.

Recently, endogenous substances having morphine-like properties have been extracted from mammalian brain or csf. These substances, named enkephalins, have been identified by Hughes et al., *Nature,* 258, 577 (1975) as pentapeptides having the following sequences:

H-Tyr-Gly-Gly-Phe-Met-OH

H-Tyr-Gly-Gly-Phe-Leu-OH.

These compounds are referred to as methionine-enkephalin and leucine-enkephalin, respectively.

Although methionine and leucine enkephalin have been shown to exhibit analgesic activity in mice upon administration intracerebroventricularly [Buscher et al., *Nature,* 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559–562 (1977), report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide; and (c) modification of the Phe in the 4-position by α-aza substitution, N-methylation, or hydrogenation of the aromatic ring.

In addition, Roemer et al., *Nature* 268, pp. 547–549 (1977), suggest modification of the $Met^5$ to its corresponding carbinol and oxidation of the Met sulfur to the sulfoxide as useful modifications.

Another structural modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

Coy et al., U.S. Pat. No. 4,180,501, describe compounds comprising two D-amino $acid^2$-enkephalins or two tetrapeptides having the first four amino acid residues of a D-amino $acid^2$-enkephalin joined at their carboxyl termini through the two amino functions of lysine.

A class of enkephalin analogs having a high level of analgesic activity has now been discovered. These analogs comprise two pentapeptides or tetrapeptide amides joined by $-(CH_2)_n$.

SUMMARY OF THE INVENTION

Thus, this invention relates to a class of compounds having the formula

[R-Tyr-A-Gly-(N-R$_1$)Phe(p-Y)-X]$_2$-(CH$_2$)$_n$

in which

R is hydrogen or methyl;

A is the residue of a D-amino acid selected from the group consisting of Ala, Abu, Ser, Thr, and Met;

$R_1$ is hydrogen, $C_1$–$C_3$ primary alkyl, cyclopropylmethyl, or allyl;

Y is hydrogen or fluoro;

n is an integer from 1 to 10; and

X is —NH— or a group of the formula

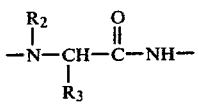

in which $R_2$ is hydrogen or $C_1$–$C_3$ primary alkyl; $R_3$ is phenyl, 2-methylthioethyl, or isobutyl; or $R_2$ and $R_3$ taken together are —CH$_2$—CH$_2$—CH$_2$—; subject to the limitation that, when $R_2$ is other than hydrogen, $R_1$ is hydrogen.

DETAILED DESCRIPTION OF THE INVENTION

As indicated above, the compounds of this invention have the following structure:

[R-Tyr-A-Gly-(N-R$_1$)Phe(p-Y)-X]$_2$-(CH$_2$)$_n$

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, formic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the above structure, the compounds are tetrapeptide or pentapeptide dimers. The C-terminal portion of the tetrapeptide or pentapeptide moiety is an amide, and two of these are joined at the amide moiety through a $-(CH_2)_n$ group.

The stereoconfiguration of the compounds of this invention is an essential feature thereof. For the sake of convenience, the amino acid residues of the tetrapeptide or pentapeptide portions of the compounds of this invention are numbered sequentially beginning with the residue at the terminal amino function. The chirality of the amino acid residues, reading from Position 1 through Position 4 for the tetrapeptide or the pentapeptide is L, D, none, and L. The residue in Position 3 is a glycine moiety, and, thus, no chirality as to this residue exists. When the peptide portion of the compounds of this invention is a pentapeptide, the chirality of Position 5 (the C-terminal position) is that which is consistent with and corresponds to the corresponding putative L-amino acid residue or the corresponding putative D-amino acid residue including, of course, the racemic mixture of both.

The groups $R_1$ and $R_2$ as used herein are defined to include the group "$C_1$–$C_3$ primary alkyl". By the term "$C_1$–$C_3$ primary alkyl" is meant methyl, ethyl, and n-propyl.

With respect to the particular position residues of the tetrapeptide and pentapeptide portions of the compounds of this invention, the following considerations prevail:

(A) Position 1

This position represents the amino-terminal portion of the peptide. The residue is that which results from L-tyrosine. The residue can be N-unsubstituted, in which case R is hydrogen, or N-substituted, in which case R is methyl. Preferably, R is hydrogen.

(B) Position 2

The amino acid residue which is present in the second position of the peptide portion of the compounds of this invention must be the D stereoisomer and is any of Ala, Abu, Ser. Thr, and Met. Each of the foregoing is an α-amino acid, and the group ($R_4$) bonded to the α-carbon is as follows: D-alanine (Ala) ($R_4$ is methyl), D-α-aminobutyric acid (Abu) ($R_4$ is ethyl), D-methionine (Met) ($R_4$ is 2-methylthioethyl), D-serine (Ser) ($R_4$ is hydroxymethyl), and D-threonine (Thr) ($R_4$ is 1-hydroxyethyl). Preferably, $R_4$ is 1-hydroxyethyl or methyl, i.e., A is the residue derived from D-alanine or D-threonine. Most preferably, A is the residue derived from D-alanine.

(C) Position 3

The amino acid residue present in this position is that derived from glycine (Gly).

(D) Position 4

The amino acid residue present in this position is that derived from L-phenylalanine (Phe) or L-p-fluorophenylalanine [Phe(F)]. The residue can be either unsubstituted or substituted at the amino nitrogen ($R_1$). In the event that the residue is N-substituted, it is N-methyl, N-ethyl, N-n-propyl, N-cyclopropylmethyl, or N-allyl. Preferably, when $R_1$ is other than hydrogen, it is ethyl, cyclopropylmethyl, or allyl, and, most preferably, is ethyl.

(E) Position 5

In those instances in which X is

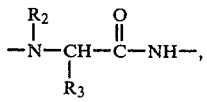

the peptide portion of the compounds of this invention is a pentapeptide. The amino acid residue in the thereby defined Position 5 is phenylglycine (Pgl) ($R_3$ is phenyl), methionine (Met) ($R_3$ is 2-methylthioethyl), leucine (Leu) ($R_3$ is isobutyl), or proline (Pro) ($R_2$ and $R_3$ taken together are —$CH_2CH_2CH_2$—). Preferably, the residue is Pgl or Met, and, most preferably, is Met.

The chirality of the residue is L-, D-, or the D,L-mixture. Preferably, the chirality is L-.

With respect to those compounds of this invention in which the peptide portion is a pentapeptide, the following subclasses are preferred:

(1) Those compounds in which the C-terminal amino acid residue is Met, and, more preferably, those having a Met residue in which $R_2$ is $C_1$-$C_3$ primary alkyl, and, preferably, is methyl; and (2) When $R_2$ is hydrogen, those compounds in which $R_1$ is other than hydrogen, and, preferably, is ethyl, cyclopropylmethyl, or allyl.

The term "n" defines the number of methylene units present in the group through which the peptide portions of the compounds of this invention are joined. The level and kind of analgesic activity, i.e., whether largely central or peripheral, are related to the length of the connecting chain. If central activity is desired, the chain preferably is relatively short; n is 1 or 2, and preferably 1. On the other hand, if peripheral activity is desired, the connecting chain preferably is lengthened; n is 4 to 10. Moreover, if the peptide portion is a tetrapeptide and peripheral activity is desired, n preferably is 7 to 9, whereas, if the peptide portion is a pentapeptide and peripheral activity is desired, n preferably is 4 to 8.

In this specification, the following abbreviations, most of which are well known and are commonly used in the art, are employed:

Abu—α-aminobutyric acid
Ala—alanine
Gly—glycine
Leu—leucine
Met—methionine
Pgl—phenylglycine
Phe—phenylalanine
Phe(F)—p-fluorophenylalanine
Pro—proline
Ser—serine
Thr—threonine
Tyr—tyrosine
Ac—acetyl
Al—allyl
Cp—cyclopropylmethyl
Me—methyl
Et—ethyl
Ip—isopropyl
Pr—n-propyl
Bu—n-butyl
i-Bu—isobutyl
t-Bu—t-butyl
s-Bu—sec-butyl
Boc—t-butyloxycarbonyl
Bzl—benzyl
Cbz—benzyloxycarbonyl
DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl
IBCF—isobutyl chloroformate
NMM—N-methylmorpholine
18-crown-6—1,4,7,10,13,16-hexaoxacyclooctadecane Examples of typical compounds of this invention include the following:

[H-L-Tyr-D-Ala-Gly-L-(N-Me)Phe-L-Met-NH]$_2$-(CH$_2$);

[H-L-Tyr-D-Ala-Gly-L-Phe(F)-L-(N-Me)Met-NH]$_2$-(CH$_2$)$_2$;

[H-L-Tyr-D-Abu-Gly-L-Phe-L-(N-Et)Met-NH]$_2$-(CH$_2$)$_4$;

[H-L-Tyr-D-Abu-Gly-L-Phe-D-(N-Me)Met-NH]$_2$-(CH$_2$)$_8$;

[H-L-Tyr-D-Ser-Gly-L-Phe-L-(N-Me)Met-NH]$_2$-(CH$_2$)$_3$;

[H-L-Tyr-D-Ser-Gly-L-(N-Et)Phe(F)-L-Met-NH]$_2$-(CH$_2$)$_{10}$;

[H-L-Tyr-D-Thr-Gly-L-Phe-D-(N-Et)Met-NH]$_2$-(CH$_2$)$_9$;
[H-L-Tyr-D-Thr-Gly-L-(N-Pr)Phe-L-Pgl-NH]$_2$-(CH$_2$)$_5$;
[H-L-Tyr-D-Met-Gly-L-Phe-L-(N-Me)Met-NH]$_2$-(CH$_2$)$_6$;
[H-L-Tyr-D-Met-Gly-L-Phe-D-Pro-NH]$_2$-(CH$_2$)$_7$;
[H-L-Tyr-D-Ala-Gly-L-(N-Cp)Phe-L-Met-NH]$_2$-(CH$_2$)$_4$;
[H-L-Tyr-D-Abu-Gly-L-Phe-L-(N-Pr)Met-NH]$_2$-(CH$_2$)$_3$;
[H-L-Tyr-D-Ser-Gly-L-Phe-L-(N-Me)Met-MH]$_2$-(CH$_2$)$_9$;
[H-L-Tyr-D-Thr-Gly-L-Phe(F)-D-(N-Pr)Met-NH]$_2$-(CH$_2$)$_6$;
[H-L-Tyr-D-Ala-Gly-L-Phe-L-(N-Et)Pgl-NH]$_2$-(CH$_2$)$_7$;
[H-L-Tyr-D-Ala-Gly-L-Phe-L-(N-Pr)Met-NH]$_2$-(CH$_2$)$_9$;
[H-L-Tyr-D-Ala-Gly-L-Phe-D-(N-Pr)Met-NH]$_2$-(CH$_2$)$_2$;
[H-L-Tyr-D-Ala-Gly-L-(N-Al)Phe-L-Pgl-NH]$_2$-(CH$_2$)$_4$;
[H-L-Tyr-D-Ala-Gly-L-Phe-L-(N-Me)Leu-NH]$_2$-(CH$_2$)$_5$;
[H-L-Tyr-D-Ala-Gly-L-(N-Et)Phe-D-Leu-NH]$_2$-(CH$_2$)$_2$;
[H-L-Tyr-D-Ala-Gly-L-Phe-L-(N-Me)Leu-NH]$_2$-(CH$_2$)$_8$;
[H-L-Tyr-D-Ala-Gly-L-Phe-L-(N-Me)Leu-NH]$_2$-(CH$_2$)$_4$;
[H-L-Tyr-D-Ala-Gly-L-Phe(F)-L-(N-Et)Leu-NH]$_2$-CH$_2$)$_2$;
[H-L-Tyr-D-Ala-Gly-L-Phe-D-Pro-NH]$_2$-(CH$_2$)$_2$;
[H-L-Tyr-D-Ser-Gly-L-Phe-L-Pro-NH]$_2$-(CH$_2$)$_4$;
[H-L-Tyr-D-Abu-Gly-L-Phe-L-(N-Me)Leu-NH]$_2$-(CH$_2$)$_8$;
[H-L-Tyr-D-Thr-Gly-L-Phe-L-(N-Et)Leu-NH]$_2$-(CH$_2$)$_7$;
[H-L-Tyr-D-Met-Gly-L-Phe(F)-D-(N-Me)Leu-NH]$_2$-(CH$_2$);
[H-L-Tyr-D-Ala-Gly-L-(N-Cp)Phe-L-Leu-NH]$_2$-(CH$_2$)$_2$;
[H-L-Tyr-D-Ala-Gly-L-Phe-L-Pro-NH]$_2$-(CH$_2$)$_4$;
[H-L-Tyr-D-Ala-Gly-L-Phe-L-Pro-NH]$_2$-(CH$_2$)$_{10}$;
[H-L-Tyr-D-Ala-Gly-L-Phe-D-(N-Me)Leu-NH]$_2$-(CH$_2$)$_{10}$;
[H-L-Tyr-D-Ala-Gly-L-(N-Al)Phe-L-Pgl-NH]$_2$-(CH$_2$)$_4$;
[H-L-Tyr-D-Ser-Gly-L-Phe(F)-L-(N-Me)Met-NH]$_2$-(CH$_2$)$_3$;
[H-L-Tyr-D-Abu-Gly-L-Phe-L-(N-Me)Leu-NH]$_2$-(CH$_2$);
[H-L-Tyr-D-Met-Gly-L-Phe-L-(N-Me)Met-NH]$_2$-(CH$_2$)$_7$;
[H-L-Tyr-D-Met-Gly-L-Phe-D-(N-Et)Met-NH]$_2$-(CH$_2$)$_2$;
[H-L-Tyr-D-Met-Gly-L-Phe-L-(N-Et)Met-NH]$_2$-(CH$_2$)$_8$;
[H-L-Tyr-D-Thr-Gly-L-(N-Me)Leu-NH]$_2$-(CH$_2$)$_6$;
[(N-Me)-L-Tyr-D-Ser-Gly-L-Phe-L-Pro-NH]$_2$-(CH$_2$)$_2$;
[(N-Me)-L-Tyr-D-Ala-Gly-L-(N-Et)Phe-L-Leu-NH]$_2$-(CH$_2$)$_4$;
[(N-Me)-L-Tyr-D-Ala-Gly-L-Phe(F)-L-Pro-NH]$_2$-(CH$_2$)$_5$;
[(N-Me)-L-Tyr-D-Thr-Gly-L-(N-Et)Phe-L-Pgl-NH]$_2$-(CH$_2$)$_5$;
[(N-Me)-L-Tyr-D-Abu-Gly-L-Phe-L-(N-Me)Met-NH]$_2$-(CH$_2$)$_3$;
[(N-Me)-L-Tyr-D-Ala-Gly-L-Phe-L-(N-Me)Leu-NH]$_2$-(CH$_2$)$_8$;
[(N-Me)-L-Tyr-D-Ala-Gly-L-Phe-L-Pro-NH]$_2$-(CH$_2$)$_2$;
[(N-Me)-L-Tyr-D-Ala-Gly-L-Phe-D-Pro-NH]$_2$-(CH$_2$);
[(N-Me)-L-Tyr-D-Abu-Gly-L-Phe(F)-L-(N-Et)Leu-NH]$_2$-(CH$_2$)$_3$;
[(N-Me)-L-Tyr-D-Ser-Gly-L-(N-Et)Phe-L-Pgl-NH]$_2$-(CH$_2$)$_6$;
[(N-Me)-L-Tyr-D-Met-Gly-L-Phe-L-Pro-NH]$_2$-(CH$_2$)$_7$;
[(N-Me)-L-Tyr-D-Abu-Gly-L-Phe-L-(N-Pr)Met-NH]$_2$-(CH$_2$)$_2$;
[H-L-Tyr-D-Met-Gly-L-Phe-NH]$_2$-(CH$_2$)$_2$;
[H-L-Tyr-D-Ser-Gly-L-Phe(F)-NH]$_2$-(CH$_2$);
[(N-Me)-L-Tyr-D-Thr-Gly-L-Phe-NH]$_2$-(CH$_2$)$_2$;
[(N-Me)-L-Tyr-D-Abu-Gly-L-Phe-NH]$_2$-(CH$_2$)$_3$;
[(N-Me)-L-Tyr-D-Ala-Gly-L-(N-Et)Phe(F)-NH]$_2$-(CH$_2$);
[H-L-Tyr-D-Ala-Gly-L-(N-Me)Phe-NH]$_2$-(CH$_2$)$_{10}$;
[H-L-Tyr-D-Ala-Gly-L-(N-Me)Phe-NH]$_2$-(CH$_2$)$_3$;
[H-L-Tyr-D-Ala-Gly-L-(N-Et)Phe-NH]$_2$-(CH$_2$)$_4$;
[H-L-Tyr-D-Ala-Gly-L-(N-Al)Phe-NH]$_2$-(CH$_2$)$_4$;
[H-L-Tyr-D-Ala-Gly-L-(N-Pr)Phe(F)-NH]$_2$-(CH$_2$)$_8$;
[H-L-Tyr-D-Ala-Gly-L-(N-Me)Phe-NH]$_2$-(CH$_2$)$_3$;
[H-L-Tyr-D-Ala-Gly-L-(N-Et)Phe-NH]$_2$-(CH$_2$)$_5$;
[H-L-Tyr-D-Ala-Gly-L-(N-Et)Phe-NH]$_2$-(CH$_2$);
[H-L-Tyr-D-Ala-Gly-L-Phe-NH]$_2$-(CH$_2$)$_{10}$;
[(N-Me)-L-Tyr-D-Ala-Gly-L-(N-Et)Phe-NH]$_2$-(CH$_2$)$_4$;
[(N-Me)-L-Tyr-D-Thr-Gly-L-Phe(F)-NH]$_2$-(CH$_2$)$_2$;
[(N-Me)-L-Tyr-D-Ala-Gly-L-Phe-NH]$_2$-(CH$_2$)$_9$;
[H-L-Tyr-D-Ala-Gly-L-(N-Al)Phe-NH]$_2$-(CH$_2$)$_4$;
[H-L-Tyr-D-Abu-Gly-L-Phe-NH]$_2$-(CH$_2$)$_4$;
[(N-Me)-L-Tyr-D-Abu-Gly-L-Phe-NH]$_2$-(CH$_2$)$_2$;
[H-L-Tyr-D-Ser-Gly-L-Phe-NH]$_2$-(CH$_2$)$_6$;
[H-L-Tyr-D-Met-Gly-L-(N-Et)Phe-NH]$_2$-(CH$_2$)$_5$;
[(N-Me)-L-Tyr-D-Met-Gly-L-Phe-NH]$_2$-(CH$_2$);
[H-L-Tyr-D-Ser-Gly-L-(N-Cp)Phe-NH]$_2$-(CH$_2$)$_3$;
[(N-Me)-L-Tyr-D-Thr-Gly-L-Phe(F)-NH]$_2$-(CH$_2$)$_2$;
[H-L-Tyr-D-Ala-Gly-L-(N-Pr)Phe-NH]$_2$-(CH$_2$)$_7$;
[(N-Me)-L-Tyr-D-Ala-Gly-L-(N-Al)Phe-NH]$_2$-(CH$_2$)$_3$;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized via an N,N'-α,ω-alkanediylbis-amide of the C-terminal amino acid of the intended peptide portion. This bis-amide can be prepared from the corresponding symmetrical anhydride in accordance with the following scheme using an N-protected amino acid as starting material, Z being the α-carbon substituent:

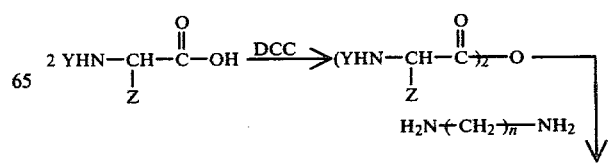

-continued

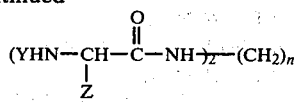

The resulting N,N'-α,ω-alkanediylbis-amide then can be treated by classical solution phase synthesis to produce the compounds of this invention. This methodology, of course, involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. the free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others, for example, benzyloxycarbonyl, can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the following sequence which omits (AA)₅ and uses the Phe symmetrical anhydride.

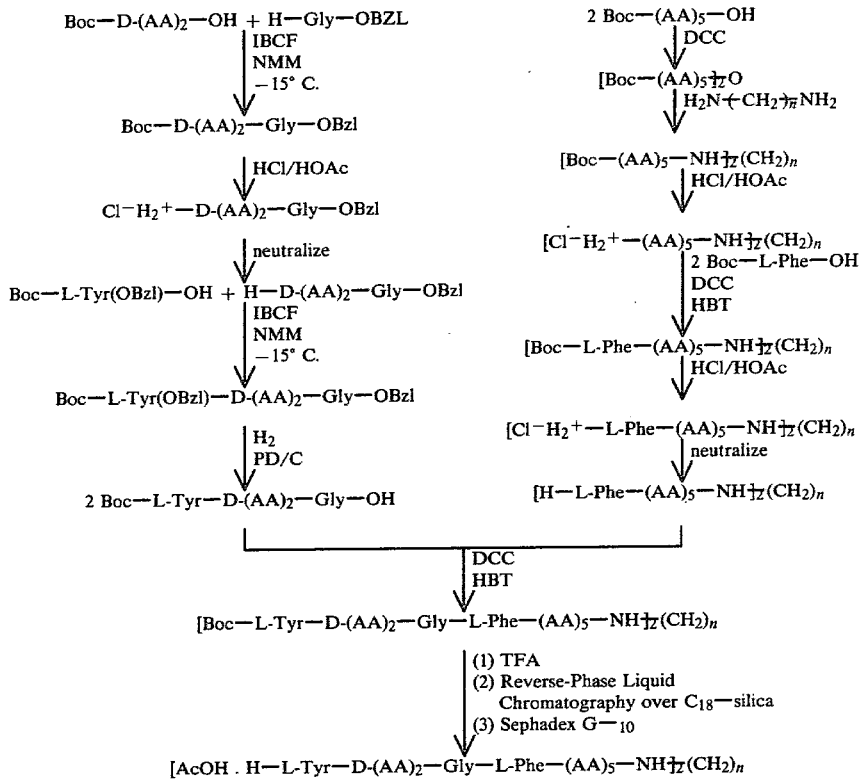

hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of an unprotected tyrosyl residue.

Of the classical solution methods, a preferred specific method for preparing the compounds of this invention involves coupling a separately prepared N-terminal tripeptide with a separately prepared N,N'-α,ω-alkanediylbis-amide of the C-terminal amino acid (when X is —NH—) or the C-terminal dipeptide (when X is

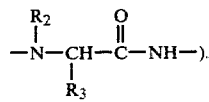

The general sequence, illustrating preparation of a compound of this invention in which X is

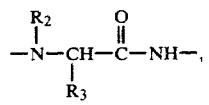

can be depicted as follows. In the sequence, the symbol AA represents an amino acid residue, and the number appended to the symbol AA represents the position of the amino acid in the ultimate peptide product sequence. Those compounds of this invention in which X is —NH— can be prepared by simplified version of the The above represents only one sequence for preparing compounds of this invention. Other sequences are available. Another method which can be employed involves the step-wise, sequential addition of single amino acids in construction of the peptide chain beginning with the C-terminal amino acid moiety. Reaction techniques such as those described above are employed in this as well as any other contemplated preparative sequence.

In certain of the compounds of this invention, one or more of the groups R, R₁, and R₂ are, variously, alkyl, allyl, or cyclopropylmethyl. In these instances, the appropriate N-substituted amino acid is employed in the preparative sequence. Any of the N-monosubstituted amino acids can be prepared as follows using an N-protected amino acid as starting material:

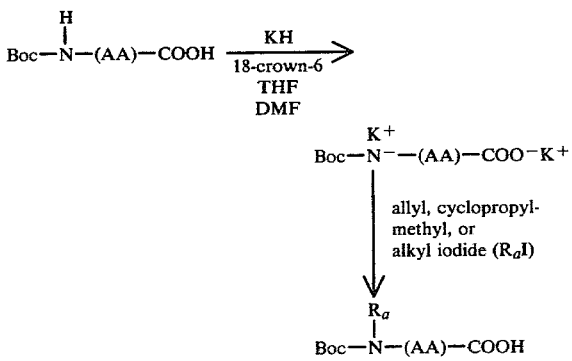

As the above sequence indicates, the amino acid first is treated with potassium hydride in the presence of a suitable crown ether to generate the dianion. The intermediate then is treated with the appropriate allyl, cyclopropylmethyl, or alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even in the event that excessive racemization does occur, the product can be purified by recrystallization as the salt of a suitable chiral amine, for example, as the salt of d(+) α-phenylethylamine.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, the intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispersing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 10 μg. to about 2 mg. per kilogram body weight of the recipient, and, preferably, from about 100 μg. to about 500 μg. per kilogram body weight, when administered intramuscularly or subcutaneously, and from about 1 μg. to about 200 μg. per kilogram body weight of the recipient, and, preferably, from about 3 μg. to about 50 μg. per kilogram body weight, when administered intravenously. When administered orally, the dosage generally will range from about 1 mg. to about 500 mg. per kilogram body weight of the recipient, and, preferably, from about 50 μg. to about 200 mg. per kilogram body weight, and, more preferably, from about 50 mg. to about 100 mg. per kilogram body weight.

The following examples are provided to illustrate the preparation and activity of the compounds of this invention. They are not intended to be limiting upon the scope thereof.

EXAMPLE 1

Preparation of N,N'-1,4-Butanediylbis-[L-tyrosyl-D-alanyl-glycyl-L-phenylalanylamide], Diacetate Salt

A.

N,N'-1,4-Butanediylbis-[N$^\alpha$-t-butyloxycarbonyl-L-phenylalanylamide]

To a chilled (0° C.) solution of Boc-phenylalanine (5.31 g.; 20.0 mmol.) dissolved in methylene chloride (15 ml.) was added a chilled (10° C.) solution of DCC (2.06 g.; 10.0 mmol.) in methylene chloride (15 ml.). The resultant mixture was stirred under a CaSO$_4$ drying tube at 0° C. for 0.5 hour. The reaction mixture was filtered to remove dicyclohexylurea (DCU).

To the resulting clear, colorless filtrate was added 1,4-diaminobutane (0.35 g., 4.0 mmol.), and the resultant mixture was stirred (1.0 hour) at room temperature under a CaSO$_4$ drying tube. The mixture was filtered to give 1.21 g. of title compound contaminated with Boc-Phe. An additional lot (0.63 g.) of crude title compound was obtained by ethyl acetate trituration of the solid obtained from the removal of the methylene chloride filtrate in the preceding filtration. The two crops of crude title compound were combined and recrystallized from chloroform/diethyl ether to give 1.61 g. (69%) of pure title compound.

Analysis, Calculated for C$_{32}$H$_{46}$N$_4$O$_6$ (582.747): C, 65.96; H, 7.96; N, 9.61. Found: C, 66.08; H, 8.14; N, 9.45.

B. N,N'-1,4-Butanediylbis-[L-phenylalanylamide], Ditrifluoroacetate Salt

To the compound from Part A (1.34 g., 2.3 mmol.) were added anisole (1.0 ml.), triethylsilane (1.0 ml.), and trifluoroacetic acid (10 ml.). The resulting solution was stirred under a CaSO$_4$ drying tube at room temperature for 0.5 hours after which the reaction mixture was concentrated in vacuo to a yellow oil. Ether (450 ml.) was added to the yellow oil, and the resulting precipitate was collected by filtration and dried in vacuo to give 1.20 grams (85%) of crude title compound.

Analysis, Calculated for C$_{26}$H$_{32}$F$_6$N$_4$O$_6$ (610.556): C, 51.15; H, 5.28; N, 9.18. Found: C, 50.89; H, 5.38; N, 9.37.

C.

N,N'-1,4-Butanediylbis-[N$^{\alpha\text{-}t\text{-}butyloxycarbonyl\text{-}L\text{-}tyrosyl\text{-}D\text{-}ala\text{-}nyl\text{-}glycyl\text{-}L\text{-}phenylalanylamide}}$]

The dicyclohexylamine salt of Boc-Tyr-D-Ala-Gly-OH (1.94 g.; 3.29 mmol.) was suspended in DMF (15 ml.), and cooled in an ice-salt bath to −15° C. To this mixture were added isobutyl chloroformate (0.449 g.; 3.29 mmol.), and, after two minutes, a chilled (−15° C.) solution of the product from Part B (1.00 g.; 1.64 mmol.)

and N-methylmorpholine (0.332 g.; 3.28 mmol.) in DMF (5 ml.). The resultant mixture was allowed to stir at −15° C. (1 hour) and at room temperature (27 hours) under a CaSO$_4$ drying tube. The reaction mixture was filtered to remove insolubles, and the filtrate was concentrated in vacuo to give a yellow residue. The residue was suspended between water (100 ml.) and ethyl acetate (200 ml.). The water was drawn off to remove the yellow color, and the ethyl acetate suspension was washed with water (100 ml.). The ethyl acetate layer was filtered to give 0.607 g. (32%) of the title compound.

Analysis, Calculated for C$_{60}$H$_{80}$N$_{10}$O$_{14}$(1165.365): C, 61.85; H, 6.92; N, 12.02. Found: C, 61.69; H, 7.04; N, 11.95.

Amino Acid Analysis:

| Tyr | Ala | Gly | Phe | % Peptide |
|---|---|---|---|---|
| 0.95 | 1.05 | 1.05 | 0.94 | 97 |

D.

N,N'-1,4-Butanediylbis-[L-tyrosyl-D-alanyl-glycyl-L-phenylalanylamide], Ditrifluoroacetate Salt To the product from Part C (0.564 g.; 0.484 mmol.) were added anisole (1.0 ml.), triethylsilane (1.0 ml.), and trifluoroacetic acid (10 ml.). The resulting solution was stirred under a CaSO$_4$ drying tube at room temperature for 1.0 hours after which the reaction mixture was concentrated in vacuo to a yellow oil. Ether (500 ml.) was added to the yellow oil, and the resulting precipitate was collected by filtration and dried in vacuo to give 0.484 grams (85%) of crude title compound.

E.

N,N'-1,4-Butanediylbis-[L-tyrosyl-D-alanyl-glycyl-L-phenylalanylamide], Diacetate Salt The crude peptide from Part D was chromatographed over a column (3.8×585 cm.) of reverse-phase (C$_{18}$) silica gel at low pressure (84 psig) with 25 percent acetonitrile in 0.1 N ammonium acetate. After collecting eighty 1.5 minute fractions of 18 ml. each, fractions 81–140 were pooled and lyophilized to give the final product, which was chromatographed over a Sephadex G-10 column (2.5×100 cm.) in 0.2 N acetic acid to remove ammonium acetate. The eluate was monitored by UV absorbance at 280 nm., and 3 minute (8.4 ml.) fractions were collected. Fractions 35–70 were combined and lyophilized to give 0.339 grams (70%) of the title compound.

Analysis, Calculated for C$_{54}$H$_{72}$N$_{10}$O$_{14}$(1085.234): C, 59.77; H, 6.69; N, 12.91. Found: C, 59.51; H, 6.47; N, 12.69.

Amino Acid Analysis:

|  | Tyr | Ala | Gly | Phe | % Peptide |
|---|---|---|---|---|---|
| (1) | 1.00 | 1.00 | 1.00 | 1.00 | 89 |
| (2) | 1.00 | 1.01 | 1.01 | 0.98 | 91 |

$[\alpha]_D^{25}$ + 56.8° (c = 0.5, 1N HCl).
$[\alpha]_{365}^{25}$ + 214.9° (c = 0.5, 1N HCl).

EXAMPLE 2

Preparation of
N,N'-1,8-Octanediylbis-[L-tyrosyl-D-alanyl-glycyl-L-phenylalanylamide], Diacetate Salt This product was prepared in accordance with the procedure of Example 1 with one modification. Following the C$_{18}$-silica gel chromatography of the crude dimer, the resultant lyophilized white powder was dissolved in 0.2 N acetic acid. The solution was filtered to remove insolubles, and the filtrate was lyophilized to obtain 0.882 g. of the title compound as a white powder.

Analysis, Calculated for C$_{58}$H$_{80}$N$_{10}$O$_{14}$(1141.343): C, 61.04; H, 7.07; N, 12.27. Found: C, 60.90; H, 6.78; N, 12.40.

Amino Acid Analysis:

|  | Tyr | Ala | Gly | Phe | % Peptide |
|---|---|---|---|---|---|
| (1) | 1.00 | 1.00 | 1.00 | 0.99 | 87 |
| (2) | 1.00 | 1.00 | 0.99 | 1.03 | 89 |

$[\alpha]_D^{25}$ + 53.77° (c = 0.3, 1N HCl).
$[\alpha]_{365}^{25}$ + 195.41° (c = 0.3, 1N HCl).

EXAMPLE 3

Preparation of
N,N'-Methanediylbis-[L-tyrosyl-D-alanyl-glycyl-L-phenylalanyl-L-(N$^\alpha$-methyl)methioninamide], Diacetate Salt

A.

N,N'-Methanediylbis-[L-(N$^\alpha$-methyl)methioninamide], Dihydrochloride Salt

To a chilled (0° C.) solution of N$^\alpha$-t-butyloxycarbonyl-L-(N$^\alpha$-methyl)methionine (5.63 g.; 20.0 mmol.) dissolved in methylene chloride (25 ml.) was added a chilled (0° C.) solution of DCC (2.06 g., 10.0 mmol.) in methylene chloride (5 ml.). The resultant mixture was stirred under a CaSO$_4$ drying tube at 0° C. for 0.5 hours. The reaction mixture was filtered to remove dicyclohexylurea (DCU).

To the resultant clear, colorless filtrate were added diaminomethane dihydrochloride salt (0.476 g.; 4.0 mmol.) and diisopropylethylamine (1.03 g.; 8.0 mmol.) dissolved in methylene chloride (5 ml.), and the resultant mixture was stirred (17 hours) at room temperature under a CaSO$_4$ drying tube. The reaction mixture was concentrated in vacuo to give a pale yellow oil. The oil was dissolved in tetrahydrofuran (25 ml.), and the excess symmetrical anhydride was destroyed by stirring with 25 ml. of KHCO$_3$ solution (135 mg./ml. H$_2$O) for 15 minutes. The solution was diluted with water (75 ml.) and washed with ethyl acetate (125 ml.). The ethyl acetate layer was washed successively with 0.1 N HCl (3×50 ml.), 5% NaHCO$_3$ (3×50 ml.), and water (3×50 ml). The ethyl acetate was dried (MgSO$_4$), filtered, and concentrated in vacuo to give a slightly damp (EtOAc) white solid.

To a solution of this compound in glacial acetic acid (7.0 ml.), anisole (1.56 ml.), and triethylsilane (1.56 ml.) were added 15.6 ml. (20 mmol.) of 1.28 N HCl in acetic acid. The reaction mixture was stirred at room temperature for 50 minutes under a CaSO$_4$ drying tube, and the mixture then was diluted with 400 ml. of ether. The resulting precipitate was filtered, washed twice with ether (50 ml.) and dried in vacuo to give 1.08 grams of the title compound (66%).

B.
N,N'-Methanediylbis-[N$^\alpha$-t-butyloxycarbonyl-L-phenylalanyl-L-(N$^\alpha$-methyl)methioninamide]

To a cooled (0° C.) suspension of the product from Part A (1.08 g., 2.64 mmol.) in DMF (7 ml.) were added 0.91 ml. (5.28 mmol.) of DIEA, 1.43 g. (10.6 mmol.) of HBT, a solution of 1.40 g. (5.28 mmol.) of Boc-L-phenylalanine in 5.5 ml. of DMF, and a solution of 1.09 g. (5.28 mmol.) of DCC in 5.0 ml. of DMF. The reaction mixture was stirred in the melting ice bath under a CaSO$_4$ drying tube for 16 hours. The reaction mixture was filtered to remove dicyclohexylurea (DCU), and the filtrate was concentrated in vacuo to give a yellow slurry which was partitioned between 150 ml. of ethyl acetate and 200 ml. of water. The layers were separated, and the ethyl acetate layer was washed successively two times each with 200 ml. of water, 200 ml. of pH 10 buffer, 200 ml. of 0.1 N HCl, and 200 ml. of water. The ethyl acetate was dried (MgSO$_4$) and filtered, and the solvent was removed in vacuo to give the title compound as a sticky yellow foam which was used without further purification or characterization.

C.
N,N'-Methanediylbis-[L-phenylalanyl-L-(N$^\alpha$-methyl)-methioninamide], Ditrifluoroacetate Salt To all of the product from Part B suspended in 2.5 ml. of anisole and 2.5 ml. of triethylsilane were added 25 ml. of trifluoroacetic acid. The resulting clear, yellow solution was stirred for one hour under a CaSO$_4$ drying tube, and then was concentrated in vacuo to give a yellow oil. The oil was triturated with 1.5 liters of ether, and the precipitate was collected by filtration, washed twice with 20 ml. of ether, and dried in vacuo at 35° C. (2 hr.) to give 1.48 g. (65% overall from Part B) of the title compound free of DCU contamination, as judged by thin-layer chromatography in four solvent systems. This material was used without further purification or characterization.

D.
N,N'-Methanediylbis-[N$^\alpha$-t-butyloxycarbonyl-L-tyrosyl-D-alanyl-glycyl-L-phenylalanyl-L-(N$^\alpha$-methyl)-methioninamide]

The dicyclohexylamine salt of Boc-Tyr-D-Ala-Gly-OH (2.01 g., 3.4 mmol.) was suspended in DMF (14.5 ml.) and cooled in an ice-salt bath to −8° C. To this mixture were added isobutyl chloroformate (0.46 g., 3.4 mmol.) and, after two minutes, a chilled (−10° C.) solution of the product from Part C (1.48 g., 1.7 mmol.) and N-methylmorpholine (0.34 g., 3.4 mmol.) in DMF (9.7 ml.). The resultant mixture was allowed to stir in the melting ice-salt bath under a CaSO$_4$ drying tube (16 hours). The reaction mixture was concentrated in vacuo to give a yellow residue which was partitioned between ethyl acetate (150 ml.) and water (150 ml.).

The two layers were separated, and the water layer was washed with ethyl acetate (2×150 ml.). All ethyl acetate layers were combined and washed successively with 0.1 N HCl (3×200 ml.), 5% NaHCO$_3$ (3×200 ml.), and water (3×200 ml.). The ethyl acetate was dried (MgSO$_4$) and filtered, and the solvent was removed in vacuo to give 1.66 g. (69%) of the title compound as a yellow solid which was used without further purification or characterization.

E.
N,N'-Methanediylbis-[L-tyrosyl-D-alanyl-glycyl-L-phenylalanyl-L-(N$^\alpha$-methyl)methioninamide], Ditrifluoroacetate Salt To 1.66 grams (1.17 mmol.) of the product from Part D suspended in 2.2 ml. of anisole and 2.2 ml. of triethylsilane were added 18 ml. of trifluoroacetic acid. The resulting clear, yellow solution was stirred for 45 minutes under a CaSO$_4$ drying tube and then was concentrated in vacuo to give a yellow oil. The oil was triturated with 1.5 liters of ether, and the precipitate was collected by filtration, washed twice with 40 ml. of ether, and dried in vacuo at 35° C. to give 1.45 g. (86%) of the title compound free of DCU contamination as judged by thin-layer chromatography in four solvent systems.

F.
N,N'-Methanediylbis-[L-tyrosyl-D-alanyl-glycyl-L-phenylalanyl-L-(N-methyl)methioninamide], Diacetate Salt The product from Part E (1.45 g., 1.01 mmol.) was chromatographed at 50 psig over a C$_{18}$-silica gel column (7×67 cm.) utilizing 25% CH$_3$CN-0.1 N NH$_4$OAc as elution solvent. The column effluent was monitored by UV absorbance at 280 nm., and, after 4000 ml. had been eluted, the eluate was collected in fractions of 1.6 minutes and 22.9 ml. each. Fractions 58–107 were combined and lyophilized to give a white solid.

This solid was separated from residual buffer salts by chromatography over Sephadex G-10 utilizing 0.2 N acetic acid as elution solvent. The eluate was monitored by UV absorbance at 280 nm., and 3.0 minute (9.6 ml.) fractions were collected. Fractions 37–54 were combined and lyophilized to give 0.85 grams (59%) of the title compound.

Analysis, Calculated for C$_{63}$H$_{88}$N$_{12}$O$_{16}$S$_2$ (1,333.601): C, 56.74; H, 6.65; N, 12.60; S, 4.81. Found: C, 56.74; H, 6.75; N, 12.88; S, 4.71.

Amino Acid Analysis:

|     | Tyr  | Ala  | Gly  | Phe  | NH$_3$ | % Peptide |
|-----|------|------|------|------|--------|-----------|
| (1) | 0.99 | 1.03 | 1.00 | 0.97 | 1.03*  | 95        |
| (2) | 0.99 | 1.02 | 1.00 | 0.97 | 1.04*  | 91        |

$[\alpha]_D^{25}$ + 20.03° (c = 0.5, 1 N HCl).
$[\alpha]_{365}^{25}$ + 74.65° (c = 0.5, 1 N HCl).

*During acid hydrolysis the NH$_2$CH$_2$NH$_2$ moiety is cleaved to two moles of ammonia and one mole of carbonic acid.

EXAMPLE 4

Preparation of N,N'-1,4-Butanediylbis-[L-tyrosyl-D-alanyl-glycyl-L-phenylalanyl-L-(N$^\alpha$-methyl)methioninamide], Diformate Salt This product was prepared in accordance with the procedure of Example 3 with one modification. The elution solvent utilized for the C$_{18}$-silica gel chromatography was 30% CH$_3$CN-0.1 M triethylammonium formate. As a result, after Sephadex G-10 chromatography, there was obtained 0.231 g. of the peptide dimer as the bisformate salt which exhibited the following chracteristics:

Analysis, Calculated for C$_{64}$H$_{90}$N$_{12}$O$_{16}$S$_2$ (1,347.630): C, 57.04; H, 6.73; N, 12.47. Found: C, 56.39; H, 6.77; N, 12.81.

Amino Acid Analysis:

|     | Tyr  | Ala  | Gly  | Phe  | % Peptide |
|-----|------|------|------|------|-----------|
| (1) | 0.98 | 1.02 | 1.02 | 0.98 | 96        |
| (2) | 0.98 | 1.02 | 1.02 | 0.97 | 89        |

$[\alpha]_D^{25} + 13.78°$ (c = 0.5, 1 N HCl).
$[\alpha]_{365}^{25} + 49.61°$ (c = 0.5, 1 N HCl).

The unique analgesic activity of the compounds of this invention is demonstrated by a comparison of the relative activities shown in the mouse hot plate and the mouse vas deferens tests. In the mouse hot plate test, an upright acrylic cylinder comprising, as its base, a hot plate surface which is maintained at 52° C. is used. A mouse (Cox Standard) is given, by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table records $ED_{50}$ results obtained from this test. By the term "$ED_{50}$" is meant that dose which produces analgesia in 50% of the mice tested. Analgesia is defined as a response latency in the presence of test compound that is equal to or greater than the control response latency plus two standard deviations. The percent analgesia data are converted to probits, and the $ED_{50}$ is calculated by regression analysis of the dose-response data. Each dose response curve must have at least four points, and each point is determined using data from a minimum of ten treated mice and ten control mice.

In the mouse vas deferens test, single mouse vas deferens from mature mice (Cox, 30–40 g.) are suspended in 3 ml. of modified Kreb's solution aerated with 95% $O_2$–5% $CO_2$ and maintained at 37° C. The twitch induced by field stimulation (0.15 Hz, 1 msec., 40 V) is recorded on a polygraph via an isometric transducer. The test compound is added to the bath in 20 to 30 μl. aliquots. A dose-response curve is constructed by cumulative addition of appropriate amounts of the compound to the bath. Comparison of relative agonist potency is made on the basis of $IC_{50}$ values (concentration causing depression of 50% of the electrically evoked contraction).

The Tables following provide results for compounds of this invention when tested in the mouse hot plate and the mouse vas deferens assays. The unexpected divergency of activity between compounds of this invention and their corresponding monomers is noteworthy.

TABLE I

| [H—L-Tyr—D-Ala—Gly—L-Phe—NH]$_2$—(CH$_2$)$_n$ | | |
|---|---|---|
| Compound n | Mouse Jump $ED_{50}$, mg./kg. | Mouse Vas Deferens $IC_{50}$, nM |
| 4 | 5.5 | 74.2 |
| 8 | >30 | 67.0 |
| —* | 0.85 | 189 |

*H—L-Tyr—D-Ala—Gly—L-Phe—NH$_2$.

TABLE II

| [H—L-Tyr—D-Ala—Gly—L-Phe—L-(N—Me)Met—NH]$_2$—(CH$_2$)$_n$ | | |
|---|---|---|
| Compound n | Mouse Jump $ED_{50}$, mg./kg. | Mouse Vas Deferens $IC_{50}$, nM |
| 1 | 0.370 | 2.83 |
| 4 | 9.85 | 0.51 |
| —* | 0.363 | 12.2 |

*H—L-Tyr—D-Ala—Gly—L-Phe—L-(N—Me)Met—NH$_2$.

I claim:
1. A compound of the formula

[R-Tyr-A-Gly-(N-R$_1$)Phe(p-Y)-X]$_2$-(CH$_2$)$_n$ in which
R is hydrogen or methyl;
A is the residue of a D-amino acid selected from the group consisting of Ala, Abu, Ser, Thr, and Met;
R$_1$ is hydrogen, C$_1$–C$_3$ primary alkyl, cyclopropylmethyl, or allyl;
Y is hydrogen or fluoro;
n is an integer from 1 to 10; and
X is —NH— or a group of the formula

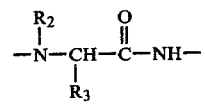

in which R$_2$ is hydrogen or C$_1$–C$_3$ primary alkyl; R$_3$ is phenyl, 2-methylthioethyl, or isobutyl; or R$_2$ and R$_3$ taken together are —CH$_2$—CH$_2$—CH$_2$—; subject to the limitation that, when R$_2$ is other than hydrogen, R$_1$ is hydrogen.

2. Compound of claim 1, in which X is —NH—.
3. Compound of claim 2, in which n is 1 or 2.
4. Compound of claim 3, in which A is Ala.
5. Compound of claim 4, in which R is hydrogen and R$_1$ is ethyl.
6. Compound of claim 4, in which R is hydrogen and R$_1$ is cyclopropylmethyl.
7. Compound of claim 4, in which R is hydrogen and R$_1$ is allyl.
8. Compound of claim 4, in which R is methyl and R$_1$ is ethyl.
9. Compound of claim 4, in which R is methyl and R$_1$ is cyclopropylmethyl.
10. Compound of claim 4, in which R is methyl and R$_1$ is allyl.
11. Compound of claim 2, in which n is an integer from 4 to 10.
12. Compound of claim 2, in which n is an integer from 7 to 9.
13. Compound of claim 12, in which A is Ala.
14. Compound of claim 13, in which R is hydrogen and R$_1$ is ethyl.
15. Compound of claim 13, in which R is hydrogen and R$_1$ is cyclopropylmethyl.
16. Compound of claim 13, in which R is hydrogen and R$_1$ is allyl.
17. Compound of claim 13, in which R is methyl and R$_1$ is ethyl.
18. Compound of claim 13, in which R is methyl and R$_1$ is cyclopropylmethyl.
19. Compound of claim 13 in which R is methyl and R$_1$ is allyl.
20. Compound of claim 1, in which X is

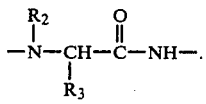

21. Compound of claim 20, in which n is 1 or 2.
22. Compound of claim 21, in which $R_1$ is hydrogen, $R_2$ is methyl, and $R_3$ is 2-methylthioethyl.
23. Compound of claim 22, in which R is hydrogen and A is Ala.
24. Compound of claim 22, in which R is methyl and A is Ala.
25. Compound of claim 21, in which $R_1$ is hydrogen, $R_2$ is methyl, and $R_3$ is isobutyl.
26. Compound of claim 25, in which R is hydrogen and A is Ala.
27. Compound of claim 25, in which R is methyl and A is Ala.
28. Compound of claim 21, in which $R_2$ is hydrogen and $R_3$ is phenyl.
29. Compound of claim 28, in which R is hydrogen and A is Ala.
30. Compound of claim 28, in which R is methyl and A is Ala.
31. Compound of claim 20, in which n is an integer from 4 to 10.
32. Compound of claim 20 in which n is an integer from 4 to 8.
33. Compound of claim 32, in which $R_1$ is hydrogen, $R_2$ is methyl, and $R_3$ is 2-methylthioethyl.
34. Compound of claim 33, in which R is hydrogen and A is Ala.
35. Compound of claim 33, in which R is methyl and A is Ala.
36. Compound of claim 32, in which $R_1$ is hydrogen, $R_2$ is methyl, and $R_3$ is isobutyl.
37. Compound of claim 36, in which R is hydrogen and A is Ala.
38. Compound of claim 36, in which R is methyl and A is Ala.
39. Compound of claim 32, in which $R_2$ is hydrogen and $R_3$ is phenyl.
40. Compound of claim 39, in which R is hydrogen and A is Ala.
41. Compound of claim 39, in which R is methyl and A is Ala.

* * * * *